(12) United States Patent
Ward

(10) Patent No.: US 9,392,947 B2
(45) Date of Patent: Jul. 19, 2016

(54) BLOOD FLOW ASSESSMENT OF VENOUS INSUFFICIENCY

(75) Inventor: Leigh Cordwin Ward, Kenmore Hills (AU)

(73) Assignee: Impedimed Limited, Pinkenba, Queensland (AT)

( * ) Notice: Subject to any disclaimer, the term of this patent is extended or adjusted under 35 U.S.C. 154(b) by 660 days.

(21) Appl. No.: 12/371,498

(22) Filed: Feb. 13, 2009

(65) Prior Publication Data

US 2009/0287102 A1 Nov. 19, 2009

Related U.S. Application Data

(60) Provisional application No. 61/029,253, filed on Feb. 15, 2008.

(51) Int. Cl.
| | |
|---|---|
| *A61B 5/02* | (2006.01) |
| *A61B 5/0265* | (2006.01) |
| *A61B 5/053* | (2006.01) |
| *A61B 5/00* | (2006.01) |

(52) U.S. Cl.
CPC .............. *A61B 5/0265* (2013.01); *A61B 5/053* (2013.01); *A61B 5/4519* (2013.01)

(58) Field of Classification Search
None
See application file for complete search history.

(56) References Cited

U.S. PATENT DOCUMENTS

| | | |
|---|---|---|
| 3,316,896 A | 5/1967 | Thomasset |
| 3,851,641 A | 12/1974 | Toole et al. |
| 3,868,165 A | 2/1975 | Gonser |
| 3,871,359 A | 3/1975 | Pacela |
| 4,008,712 A | 2/1977 | Nyboer |
| 4,034,854 A | 7/1977 | Bevilacqua |
| 4,121,575 A | 10/1978 | Mills et al. |
| 4,144,878 A | 3/1979 | Wheeler |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |

(Continued)

FOREIGN PATENT DOCUMENTS

| | | |
|---|---|---|
| CA | 2231038 | 11/1999 |
| CA | 2638958 | 6/2000 |

(Continued)

OTHER PUBLICATIONS

W A McCullagh et al, IFMBE Proceedings, vol. 17, pp. 619-619, 2007.*

(Continued)

*Primary Examiner* — Etsub Berhanu
(74) *Attorney, Agent, or Firm* — Knobbe Martens Olson & Bear LLP

(57) ABSTRACT

Impedance analysis can be used to measure calf muscle pump (CMP) function in a patient. This may be done by applying electrical signals via a first set of electrodes, and measuring the impedance via a second set of electrodes. The change in impedance as the patient undergoes calf extension or exercise may be measured, and the change in impedance may then be used to assess CMP function. The change in impedance may be used to determine an indicator indicative of the volume of blood ejected by the CMP.

16 Claims, 10 Drawing Sheets

(56) References Cited

U.S. PATENT DOCUMENTS

| | | |
|---|---|---|
| 4,450,527 A | 5/1984 | Sramek |
| 4,458,694 A | 7/1984 | Sollish et al. |
| 4,468,832 A | 9/1984 | Bai et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,922,911 A | 5/1990 | Wada et al. |
| 4,942,880 A | 7/1990 | Slovák |
| 4,951,682 A | 8/1990 | Petre |
| 4,981,141 A | 1/1991 | Segalowitz |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,143,079 A | 9/1992 | Frei et al. |
| 5,197,479 A | 3/1993 | Hubelbank et al. |
| 5,199,432 A | 4/1993 | Quedens et al. |
| 5,246,008 A | 9/1993 | Meuller |
| 5,280,429 A | 1/1994 | Whithers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel |
| 5,449,000 A | 9/1995 | Libke et al. |
| 5,465,730 A | 11/1995 | Zadehoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,588,429 A | 12/1996 | Isaacson et al. |
| 5,704,355 A | 1/1998 | Bridges |
| 5,730,136 A * | 3/1998 | Laufer et al. .................. 600/454 |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 5,994,956 A | 11/1999 | Concorso |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,101,413 A | 8/2000 | Olson et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Ferrer et al. |
| 6,173,003 B1 | 1/2001 | Whikehart et al. |
| 6,228,022 B1 | 5/2001 | Friesem et al. |
| 6,228,033 B1 | 5/2001 | Koobi |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,497,659 B1 | 12/2002 | Rafert |
| 6,532,384 B1 | 3/2003 | Fukuda |
| 6,560,480 B1 | 5/2003 | Nachaliel et al. |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtk |
| 6,633,777 B2 | 10/2003 | Szopinski |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,760,617 B2 | 7/2004 | Ward et al. |
| 6,768,921 B2 | 7/2004 | Organ et al. |
| 6,845,264 B1 | 1/2005 | Skladnev et al. |
| 6,870,109 B1 | 3/2005 | Villarreal |
| 6,875,176 B2 | 4/2005 | Mourad et al. |
| 6,906,533 B1 | 6/2005 | Yoshida |
| 6,922,586 B2 | 7/2005 | Davies |
| 6,980,853 B2 * | 12/2005 | Miyoshi et al. ............... 600/547 |
| 7,130,680 B2 | 10/2006 | Kodama et al. |
| 7,132,611 B2 | 11/2006 | Gregaard et al. |
| 7,148,701 B2 | 12/2006 | Park et al. |
| 7,206,630 B1 | 4/2007 | Tarler |
| 7,212,852 B2 | 5/2007 | Smith et al. |
| D557,809 S | 12/2007 | Neverov et al. |
| 7,457,660 B2 | 11/2008 | Smith et al. |
| 7,477,937 B2 | 1/2009 | Iijima et al. |
| 7,499,745 B2 | 3/2009 | Littrup et al. |
| D603,051 S | 10/2009 | Causevic et al. |
| 7,628,761 B2 | 12/2009 | Gozani et al. |
| 7,657,292 B2 | 2/2010 | Baker et al. |
| 7,706,872 B2 | 4/2010 | Min et al. |
| 7,733,224 B2 | 6/2010 | Tran |
| 7,749,013 B2 | 7/2010 | Sato et al. |
| 7,860,557 B2 | 12/2010 | Istvan et al. |
| D641,886 S | 7/2011 | Causevic et al. |
| D647,208 S | 10/2011 | Rothman et al. |
| 8,233,617 B2 | 7/2012 | Johnson et al. |
| 8,233,974 B2 | 7/2012 | Ward et al. |
| D669,186 S | 10/2012 | Gozani |
| D669,187 S | 10/2012 | Gozani |
| D674,096 S | 1/2013 | Gaw et al. |
| 8,467,865 B2 | 6/2013 | Gregory et al. |
| D718,458 S | 11/2014 | Vosch et al. |
| D719,660 S | 12/2014 | Vosch et al. |
| D728,801 S | 5/2015 | Machon et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson et al. |
| 2001/0025139 A1 | 9/2001 | Pearlman |
| 2002/0020138 A1 | 2/2002 | Walker et al. |
| 2002/0022787 A1 | 2/2002 | Takehara et al. |
| 2002/0035334 A1 | 3/2002 | Meij et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0109621 A1 | 8/2002 | Khair et al. |
| 2002/0111559 A1 | 8/2002 | Kurata et al. |
| 2002/0123694 A1 | 9/2002 | Organ et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |
| 2003/0036713 A1 | 2/2003 | Bouton et al. |

(56) References Cited

U.S. PATENT DOCUMENTS

| | | |
|---|---|---|
| 2003/0050570 A1 | 3/2003 | Kodama et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2003/0216661 A1 | 11/2003 | Davies |
| 2004/0015095 A1 | 1/2004 | Li et al. |
| 2004/0019292 A1 | 1/2004 | Drinan et al. |
| 2004/0059220 A1 | 3/2004 | Mourad et al. |
| 2004/0059242 A1 | 3/2004 | Masuo et al. |
| 2004/0077944 A1 | 4/2004 | Steinberg et al. |
| 2004/0127793 A1 | 7/2004 | Mendlein et al. |
| 2004/0158167 A1 | 8/2004 | Smith et al. |
| 2004/0167423 A1 | 8/2004 | Pillon et al. |
| 2004/0171961 A1 | 9/2004 | Smith et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0236202 A1 | 11/2004 | Burton |
| 2004/0242987 A1 | 12/2004 | Liew et al. |
| 2004/0252870 A1 | 12/2004 | Reeves et al. |
| 2004/0253652 A1 | 12/2004 | Davies |
| 2004/0267344 A1 | 12/2004 | Stett et al. |
| 2005/0033281 A1 | 2/2005 | Bowman et al. |
| 2005/0039763 A1 | 2/2005 | Kraemer et al. |
| 2005/0049474 A1 | 3/2005 | Kellogg et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0203435 A1 | 9/2005 | Nakada |
| 2005/0203436 A1 | 9/2005 | Davies |
| 2005/0261743 A1 | 11/2005 | Kroll |
| 2006/0004300 A1 | 1/2006 | Kennedy |
| 2006/0047189 A1 | 3/2006 | Takehara |
| 2006/0070623 A1 | 4/2006 | Wilkinson et al. |
| 2006/0085048 A1 | 4/2006 | Cory et al. |
| 2006/0085049 A1 | 4/2006 | Cory et al. |
| 2006/0100532 A1 | 5/2006 | Bae et al. |
| 2006/0111652 A1* | 5/2006 | McLeod ........................ 601/15 |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0197509 A1 | 9/2006 | Kanamori et al. |
| 2006/0224079 A1 | 10/2006 | Washchuck |
| 2006/0224080 A1 | 10/2006 | Oku et al. |
| 2006/0252670 A1 | 11/2006 | Fiorucci et al. |
| 2006/0253016 A1 | 11/2006 | Baker et al. |
| 2006/0264775 A1 | 11/2006 | Mills et al. |
| 2006/0270942 A1 | 11/2006 | McAdams |
| 2007/0010758 A1 | 1/2007 | Mattiessen et al. |
| 2007/0027402 A1 | 2/2007 | Levin et al. |
| 2007/0043303 A1 | 2/2007 | Osypka et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0048786 A1 | 2/2008 | Feldkamp et al. |
| 2008/0091114 A1* | 4/2008 | Min et al. .................... 600/508 |
| 2008/0183098 A1 | 7/2008 | Denison et al. |
| 2008/0188757 A1 | 8/2008 | Rovira et al. |
| 2008/0205717 A1 | 8/2008 | Reeves et al. |
| 2008/0221411 A1 | 9/2008 | Hausmann et al. |
| 2008/0262375 A1 | 10/2008 | Brown et al. |
| 2008/0319336 A1 | 12/2008 | Ward et al. |
| 2009/0043222 A1 | 2/2009 | Chetham |
| 2009/0054952 A1 | 2/2009 | Glukhovsky et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209828 A1 | 8/2009 | Musin |
| 2009/0264776 A1 | 10/2009 | Vardy |
| 2009/0287102 A1 | 11/2009 | Ward |
| 2009/0306535 A1 | 12/2009 | Davies et al. |
| 2009/0318778 A1 | 12/2009 | Dacso et al. |
| 2010/0100146 A1 | 4/2010 | Blomqvist |
| 2010/0168530 A1 | 7/2010 | Chetham et al. |
| 2011/0025348 A1 | 2/2011 | Chetham et al. |
| 2011/0054343 A1 | 3/2011 | Chetham et al. |
| 2011/0060239 A1* | 3/2011 | Gaw ............................ 600/547 |
| 2011/0087129 A1 | 4/2011 | Chetham et al. |
| 2011/0118619 A1 | 5/2011 | Burton et al. |
| 2011/0190655 A1 | 8/2011 | Moissl et al. |
| 2011/0251513 A1 | 10/2011 | Chetham et al. |

FOREIGN PATENT DOCUMENTS

| | | |
|---|---|---|
| CA | 2613524 | 1/2007 |
| CA | 2615845 | 1/2007 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 339471 | 3/1997 |
| EP | 865763 | 9/1998 |
| EP | 0869360 | 10/1998 |
| EP | 1080686 | 3/2001 |
| EP | 1112715 | 4/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1338246 | 8/2003 |
| EP | 1452131 | 9/2004 |
| EP | 1553871 | 7/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| FR | 2486386 | 1/1982 |
| FR | 2748928 | 11/1997 |
| GB | 1441622 | 7/1976 |
| GB | 2131558 | 6/1984 |
| GB | 2260416 | 4/1993 |
| GB | 2426824 | 12/2006 |
| JP | 6-74103 | 10/1994 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 10225521 | 8/1998 |
| JP | 11070090 | 3/1999 |
| JP | 11-513592 | 11/1999 |
| JP | 2000107138 | 4/2000 |
| JP | 2000139867 | 5/2000 |
| JP | 2001-204707 | 7/2001 |
| JP | 2001224568 | 8/2001 |
| JP | 2001-245866 | 9/2001 |
| JP | 2001321352 | 11/2001 |
| JP | 2002238870 | 8/2002 |
| JP | 2002330938 | 11/2002 |
| JP | 2002350477 | 12/2002 |
| JP | 2003075487 | 3/2003 |
| JP | 2003-116803 | 4/2003 |
| JP | 2003116805 | 4/2003 |

(56) References Cited

FOREIGN PATENT DOCUMENTS

| | | |
|---|---|---|
| JP | 2003230547 | 8/2003 |
| JP | 200461251 | 2/2004 |
| JP | 2008022995 | 7/2008 |
| RU | 2112416 | 6/1998 |
| WO | WO 88-07392 | 10/1988 |
| WO | WO 93-18821 | 9/1993 |
| WO | WO 94/01040 | 1/1994 |
| WO | WO 96-01586 | 1/1996 |
| WO | WO 96-12439 | 5/1996 |
| WO | WO 96-32652 | 10/1996 |
| WO | WO 97-11638 | 4/1997 |
| WO | WO 97-14358 | 4/1997 |
| WO | WO 97-24156 | 7/1997 |
| WO | WO 98-06328 | 2/1998 |
| WO | WO 98/12983 | 4/1998 |
| WO | WO 98-23204 | 6/1998 |
| WO | WO 98-33553 | 8/1998 |
| WO | WO 00-40955 | 7/2000 |
| WO | WO 00-79255 | 12/2000 |
| WO | WO 01-50954 | 7/2001 |
| WO | WO 01-67098 | 9/2001 |
| WO | WO 02-053028 | 7/2002 |
| WO | WO 02-062214 | 8/2002 |
| WO | WO 02-094096 | 11/2002 |
| WO | WO 2004-000115 | 12/2003 |
| WO | WO 2004/002301 | 1/2004 |
| WO | WO 2004/006660 | 1/2004 |
| WO | WO 2004-026136 | 4/2004 |
| WO | WO 2004-032738 | 4/2004 |
| WO | WO 2004-043252 | 5/2004 |
| WO | WO 2004-047635 | 6/2004 |
| WO | WO 2004-047636 | 6/2004 |
| WO | WO 2004-047638 | 6/2004 |
| WO | WO 2004-049936 | 6/2004 |
| WO | WO 2004-083804 | 9/2004 |
| WO | WO 2004-098389 | 11/2004 |
| WO | WO 2004/112563 | 12/2004 |
| WO | WO 2005-010640 | 2/2005 |
| WO | WO 2005-018432 | 3/2005 |
| WO | WO 2005-027717 | 3/2005 |
| WO | WO 2005-051194 | 6/2005 |
| WO | WO 2005-122888 | 12/2005 |
| WO | WO 2006-129108 | 12/2006 |
| WO | WO 2006-129116 | 12/2006 |
| WO | WO 2007-002991 | 1/2007 |
| WO | WO 2007-002992 | 1/2007 |
| WO | WO 2007-002993 | 1/2007 |
| WO | WO 2007-009183 | 1/2007 |
| WO | WO 2007-041783 | 4/2007 |
| WO | WO 2007/045006 | 4/2007 |
| WO | WO 2007-056493 | 5/2007 |
| WO | WO 2007/105996 | 9/2007 |
| WO | WO 2008-054426 | 8/2008 |
| WO | WO 2008/119166 | 10/2008 |
| WO | WO 2008-138062 | 11/2008 |
| WO | WO 2008/149125 | 12/2008 |
| WO | WO 2009-018620 | 2/2009 |
| WO | WO 2009-036369 | 3/2009 |
| WO | WO 2009-100491 | 8/2009 |
| WO | WO 2009/100491 | 8/2009 |
| WO | WO 2011-022068 | 2/2011 |
| WO | WO 2011-050393 | 5/2011 |
| WO | WO 2011-075769 | 6/2011 |

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

Al-Hatib, F.; Patient Instrument connection errors in bioelectrical impedance measurement; Physiological Measurement; vol. 19, No. 2, pp. 285-296; May 2, 1998.

Bella, et al., Relations of Left Ventricular Mass to Fat-Free and Adipose Body Mass: The Strong Heart Study, (1998) Circulation, vol. 98, pp. 2538-2544.

Boulier, A. et al.; Fat-Free Mass Estimation by Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Bioelectrical impedance for monitoring the efficacy of lymphoedema treatment programmes; Breast Cancer Research and Treatment; vol. 38, pp. 169-176; 1996.

Cornish, B.H. et al.; Data analysis in multiple-frequency bioelectrical impedance analysis; Physiological Measurement; vol. 19, No. 2, pp. 275-283; May 1, 1998.

Cornish, B.H. et al.; Early diagnosis of lymphedema using multiple frequency bioimpedance; Lymphology; vol. 34, pp. 2-11; Mar. 2001.

Cornish, B.H. et al.; Early diagnosis of lymphoedema in postsurgery breast cancer patients; Annals New York Academy of Sciences; pp. 571-575; May 2000.

Cornish, B.H. et al.; Quantification of Lymphoedema using Multi-frequency Bioimpedance; Applied Radiation and Isotopes; vol. 49, No. 5/6, pp. 651-652; 1998.

De Luca, F. et al., Use of low-frequency electrical impedance measurements to determine phospoholipid content in amniotic fluid; Physics in Medicine and Biology, vol. 41, pp. 1863-1869, 1996.

Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.

Dines K.A. et al.; Analysis of electrical conductivity imaging; Geophysics; vol. 46, No. 7, pp. 1025-1036; Jul. 1981.

Ellis, K.J. et al; Human hydrometry: comparison of multifrequency bioelectrical impedance with 2H2O and bromine dilution; Journal of Applied Physiology; vol. 85, No. 3, pp. 1056-1062; 1998.

Forslund, A.H. et al.; Evaluation of modified multicompartment models to calculate body composition in healthy males; American Journal of Clinical Nutrition; vol. 63, pp. 856-862; 1996.

Gersing, E.; Impedance spectroscopy on living tissue for determination of the state of Organs; Bioelectrochemistry and Bioenergetics; vol. 45, pp. 145-149; 1998.

Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. at Chapel Hill; pp. 446-453; Jun. 1990.

Gudivaka R. et al; Single- and multifrequency models for bioelectrical impedance analysis of body water compartments; Applied Physiology; vol. 87, Issue 3, pp. 1087-1096; 1999.

Iacobellis, G., et al. Influence of Excess Fat on Cardiac Morphology and Function: Study in Uncomplicated Obesity, (2002) Obesity Research, vol. 10, pp. 767-773.

Jones, C.H. et al; Extracellular fluid volume determined by bioelectric impedance and serum albumin in CAPD patients; Nephrology Dialysis Transplantation; vol. 13, pp. 393-397; 1998.

Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.

(56) References Cited

OTHER PUBLICATIONS

Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.

Kanai, H. et al.; Electrical Measurement of Fluid Distribution in Legs and Arms; Medical Progress through technology; pp. 159-170; 1987.

Karason, K., et al., Impact of Blood Pressure and Insulin on the Relationship Between Body Fat and Left Ventricular Structure, (2003) European Heart Journal, vol. 24, pp. 1500-1505.

Kim, C.T. et al.; Bioelectrical impedance changes in regional extracellular fluid alterations; Electromyography and Clinical Neurophysiology; vol. 37, pp. 297-304; 1997.

Liu R. et al; Primary Multi-frequency Data Analyze in Electrical Impedance Scanning; Proceedings of the IEEE—EMBS 2005, 27th Annual International Conference of the Engineering in Medicine and Biology Society, Shanghai, China; pp. 1504-1507; , Sep. 1-4, 2005.

Lozano, A. et al.; Two-frequency impedance plethysmograph: real and imaginary parts; Medical & Biological Engineering & Computing; vol. 28, No. 1, pp. 38-42; Jan. 1990.

Lukaski, H.C. et al.; Estimation of Body Fluid Volumes Using Tetrapolar Bioelectrical Impedance Measurements; Aviation, Space, and Environmental Medicine; pp. 1163-1169; Dec. 1988.

Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.

Mattar, J.A., Application of Total Body Impedance to the Critically Ill Patient, New Horizons, vol. 4, No. 4, pp. 493-503, Nov. 1996.

McDougal D., et al.; Body Composition Measurements From Whole Body Resistance and Reactance; Surgical Forum; vol. 36, pp. 43-44; 1986.

Osterman K.S. et al.; Multifrequency electrical impedance imaging: preliminary in vivo experience in breast; Physiological Measurement; vol. 21, No. 1, pp. 99-109; Feb. 2000.

Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.

Pethig, R. et al.; The Passive Electrical Properties of Biological Systems: Their Significance in Physiology, Biophysics and Biotechnology; Physics in Medicine and Biology; vol. 32, pp. 933-970; 1987.

Piperno, G. et al.; Breast Cancer Screening by Impedance Measurements; Frontiers of Medical & Biological Engineering; vol. 2, pp. 111-117; 1990.

Rigaud, B. et al.; Bioelectrical Impedance Techniques in Medicine; Critical Reviews in Biomedical Engineering; vol. 24 (4-6), pp. 257-351; 1996.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.

Skidmore, R. et al.; A Data Collection System for Gathering Electrical Impedance Measurements from the Human Breast; Clinical Physics Physiological Measurement; vol. 8, pp. 99-102; 1987.

Sollish, B.D. et al.; Microprocessor-assisted Screening Techniques; Israel Journal of Medical Sciences; vol. 17, pp. 859-864; 1981.

Steijaert, M. et al.; The use of multi-frequency impedance to determine total body water and extracellular water in obese and lean female individuals; International Journal of Obesity; vol. 21, pp. 930-934; 1997.

Surowiec, A.J. et al.; Dielectric Properties of Brest Carcinoma and the Surrounding Tissues; IEEE Transactions on Biomedical Engineering; vol. 35, pp. 257-263; 1988.

Tedner, B.; Equipment Using Impedance Technique for Automatic Recording of Fluid-Volume Changes During Haemodialysis; Medical & Biological Engineering & Computing; pp. 285-290; 1983.

Thomas. B.J. et al.; Bioelectrical impedance analysis for measurement of body fluid volumes—A review; Journal of Clinical Engineering; vol. 17, No. 16, pp. 505-510; 1992.

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in post-mastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Yoshinaga, M., Effect of Total Adipose Weight and Systemic Hypertension on Left Ventricular Mass in Children, American Journal of Cardiology, (1995) vol. 76, pp. 785-787.

Cornish, et al., "Optimizing Electrode Sites for Segmental Bioimpedance Measurements" Physiological Measurement, Institute of Physics, 1999, pp. 241-250, vol. 20, No. 3.

Cornish, et al., "A New Technique for the Quantification of Peripheral Edema with Application in Both Unilateral and Bilateral Cases" Angiology, 2002, pp. 41-47, vol. 53, No. 1.

Fenech, et al., "Extracellular and Intracellular Volume Variations During Postural Change Measured by Segmental and Wrist-Ankle Bioimpedance Spectroscopy" IEEE Transactions on Biomedical Engineering, IEEE Service Center, 2004, pp. 166-175, vol. 51, No. 1.

Golden, et al., "Assessment of Peripheral Hemodynmics using Impedance Plethysmogrphy" Physical Therapy, 1986, pp. 1544-1547, vol. 66, No. 10.

Kim, et al., "Impedance Tomography and its Application in Deep Venous Thrombosis Detection" IEEE Engineering in Medicine and Biology Magazine, IEEE Service Center, 1989, pp. 46-49, vol. 8, No. 1.

Nawarycz, et al., "Triple-frequency Electroimpedance Method for Evaluation of Body Water Compartments" Medical & Biological Engineering & Computing, 1996, pp. 181-182, vol. 34, No. Supp. 01, Pt. 02.

Noshiro, et al., "Electrical Impedance in the Lower Limbs of Patients with Duchenne Muscular Dystrophy: A Preliminary Study" Medical & Biological Engineering & Computing, 1993, pp. 97-102, vol. 31, No. 2.

Seo, et al., "Measuring Lower Leg Swelling: Optimum Frequency for Impedance Method" Medical & Biological Engineering & Computing, 2001, pp. 185-189, vol. 39.

Seoane, et al., "Current Source for Wideband Electrical Bioimpedance Spectroscopy Based on a Single Operational Amplifier" World Congress on Medical Physics and Biomedical Engineering 2006, pp. 707-710, vol. 14.

Smith, et al., "A Pilot Study for Tissue Characterization Using Bioimpedance Mapping" 13th International Conference on Electrical Bio-impedance and the 8th Conference on Electrical Impedance Tomography 2007, pp. 146-149.

Stanton, et al., "Non-invasive Assessment of the Lymphedematous Limb" Lymphology, The International Society of Lymphology, 2000, pp. 122-135, vol. 33, No. 3.

International Search Report and Written Opinion of the International Searching Authority issued in PCT/AU2009/000163 dated Apr. 16, 2009.

(56) References Cited

OTHER PUBLICATIONS

International Search Report and Written Opinion of the International Searching Authority issued in PCT/AU2006/000922 dated Oct. 10, 2006.
International Search Report and Written Opinion of the International Searching Authority issued in PCT/AU2006/001057 dated Oct. 25, 2006.
International Search Report and Written Opinion of the International Searching Authority issued in PCT/AU2008/000034 dated Mar. 17, 2008.
International Search Report and Written Opinion of the International Searching Authority issued in PCT/AU2008/000588 dated Aug. 13, 2008.
International Search Report and Written Opinion of the International Searching Authority issued in PCT/AU2008/001521 dated Jan. 15, 2009.
International Search Report from International Application No. PCT/AU2006/000924 dated Sep. 27, 2006.
Ivorra, A., et al.; Bioimpedance dispersion width as a parameter to monitor living tissues; Physiol. Meas. 26 (2005) S165-S173.
McCullah, et al.; Bioelectrical Impedance Analysis Measures the Ejection Fraction of the Calf Muscle Pump; IFMBE Proceedings; vol. 17, pp. 616-619; 2007.
Ezenwa, B.N. et al.; Multiple Frequency System for Body Composition Measurement; Proceedings of the Annual International Conference of the Engineering in Medicine and Biology Society; vol. 15; pp. 1020-1021; 1993.
Scharfetter, H. et al.; Effect of Postural Changes on the Reliability of Volume Estimations from Bioimpedance Spectroscopy Data; Kidney International; vol. 51, No. 4, pp. 1078-2087; 1997.
Yamakoshi, K.; Non-Invasive Cardiovascular Hemodynamic Measurements; Sensors in Medicine and Health Care; pp. 107-160; 2004.

* cited by examiner

BLOOD FLOW ASSESSMENT OF VENOUS INSUFFICIENCY

CROSS-REFERENCE TO RELATED APPLICATIONS

This application claims priority to U.S. Provisional Application No. 61/029,253, filed on Feb. 15, 2008, the disclosure of which is hereby incorporated by reference in its entirety.

BACKGROUND OF THE INVENTION

The present invention relates to a method and apparatus for use in analysing impedance measurements, and in particular, to a method and apparatus for assessing calf muscle pump function using impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Venous insufficiency is a condition characterized by an inability for veins to adequately return blood to the heart. Normally, when a subject is in a standing position, the blood in the subject's leg veins is urged back towards the heart against gravity by a combination of mechanisms, such as muscular squeezing of the leg veins, and through the action of one-way valves in the veins. However, conditions can arise such as increased pressure within the veins, deep vein thrombosis (DVT), phlebitis, or the like, which lead to blood pooling in the legs.

Chronic venous disease (CVD) is common with a 3-7% prevalence, resulting in an economic cost US$1 billion per annum, and is caused by calf muscle pump (CMP) dysfunction in ⅔ of all patients.

Existing techniques for assessing CMP function include measuring the ambulatory venous pressure, which is achieved by inserting a needle into the vein on the dorsum of the foot. Whilst this is regarded as the gold standard of haemodynamic investigation, this is invasive, and it is therefore desirable to find alternative non-invasive techniques. Two such methods are air plethysmography (APG) and strain gauge plethysmography (SPG).

SPG involves placing mercury strain gauges in a silastic band around the calf muscle which are calibrated to read percentage leg volume changes, as described for example in Nicolaides AN (2000) "*Investigation of Chronic Venous Insufficiency: A Consensus Statement*" Circulation 102:126-163. These measurements are typically performed during exercise regimens to allow venous refilling time and the ejection volume to be assessed. APG uses an air bladder which surrounds the leg from the knee to the ankle. The bladder is inflated to a known pressure, with volume changes in the calf muscle being determined based on changes in pressure on the bladder during a sequence of postural changes.

However, these techniques are only of limited accuracy, and can require extensive calibration to allow useable measurements to be obtained.

One existing technique for determining biological parameters relating to a subject, such as fluid levels, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema.

US2006/0111652 describes methods for enhancing blood and lymph flow in the extremities of a human. As part of this method, impedance measurements are used to assess segmental blood flows within the limbs.

US2005/0177062 describes a system for measuring the volume, composition and the movement of electroconductive body fluids, based on the electrical impedance of the body or a body segment. This is used primarily for electromechanocardiography (ELMEC) or impedance cardiography (IKG) measurements for determining hemodynamic parameters.

SUMMARY OF CERTAIN INVENTIVE ASPECTS

Embodiments of the present invention seek to ameliorate one or more problems of the problems associated with the prior art.

In one aspect, a method for use in analysing impedance measurements performed on a subject is provided, the method including, in a processing system:
 a) determining a change in impedance, as a subject undergoes calf extension or exercise; and,
 b) determining an indicator using the change impedance, the indicator being indicative of an ejection volume to allow assessment of CMP function.

In an additional aspect, the method includes, in a processing system:
 a) determining a first impedance value prior to calf extension;
 b) determining a second impedance value following or during calf extension; and,
 c) determining the impedance change using the first and second impedance values.

In an additional aspect, the method includes, in a processing system, determining an ejection volume using the formula:

$$EV = \frac{-\rho_b L^2 \Delta R}{R_{MV}^2}$$

where:
 $\rho_b$ is the resistivity of blood;
 L is the length of the segment;
 $\Delta R$ is the change in impedance;
 $R_{MV}$ is the maximum volume impedance value.

In an additional aspect, the method includes, in a processing system:
 a) determining a third impedance value with the subject in a supine position;
 b) determining a fourth impedance value with the subject in a standing position;
 c) determining a second impedance change using the third and fourth impedance values;
 d) determining a second indicator using the second impedance change, the second indicator being indicative of a venous volume for use in assessment of CMP function.

In an additional aspect:
 a) the third impedance value is a minimum volume impedance value $R_{mv}$; and,
 b) the fourth impedance value is a maximum volume impedance value $R_{MV}$.

In an additional aspect, the method includes, in a processing system, determining a functional venous volume using the formula:

$$VV = \frac{\rho_b L^2 (R_{mv} - R_{MV})}{R_{mv} R_{MV}}$$

where:
$R_{mv}$ is the third impedance value;
$R_{MV}$ is the fourth impedance value;
$\rho_b$ is the resistivity of blood; and,
L is the length of the segment.

In an additional aspect, the method includes, in a processing system, determining at least one of:
a) an ejection volume;
b) a venous volume; and,
c) an ejection fraction.

In an additional aspect, the method includes, in a processing system:
a) comparing an indicator to a reference; and,
b) providing an indication of the results of the comparison to allow assessment of CMP function.

In an additional aspect, the reference includes at least one of:
a) an indicator determined for another calf segment of the subject;
b) a indicator determined from a sample population; and,
c) a previous indicator determined for the subject.

In an additional aspect, the impedance is measured at a measurement frequency of less than 10 kHz.

In an additional aspect, the method includes, in the processing system:
a) determining a plurality of impedance values; and,
b) determining at least one impedance parameter value from the plurality of impedance values.

In an additional aspect, the impedance parameter values include at least one of:
$R_0$ which is the resistance at zero frequency;
$R_\infty$ which is the resistance at infinite frequency; and,
$Z_c$ which is the resistance at a characteristic frequency.

In an additional aspect, the method includes, in the processing system, determining the parameter values using the equation:

$$Z = R_\infty + \frac{R_0 - R_\infty}{1 + (j\omega\tau)^{(1-\alpha)}}$$

where:
Z is the measured impedance at angular frequency $\omega$,
$\tau$ is a time constant, and
$\alpha$ has a value between 0 and 1.

In an additional aspect, the method includes, in the computer system, causing the impedance measurements to be performed.

In an additional aspect, the method includes, in the computer system:
a) causing one or more electrical signals to be applied to the subject using a first set of electrodes;
b) measuring electrical signals across a second set of electrodes applied to the subject in response to the applied one or more signals; and,
c) determining from the applied signals and the measured signals at least one measured impedance value.

In another aspect, an apparatus for use in analysing impedance measurements performed on a subject is provided, the apparatus including a processing system for:
a) determining a change in impedance, as a subject undergoes calf extension; and,
b) determining an indicator using the change impedance, the indicator being indicative of an ejection volume to allow assessment of CMP function.

In an additional aspect, the apparatus includes a processing system for:
a) causing one or more electrical signals to be applied to the subject using a first set of electrodes;
b) measuring electrical signals across a second set of electrodes applied to the subject in response to the applied one or more signals; and,
c) determining from the applied signals and the measured signals at least one measured impedance value.

In an additional aspect, the apparatus includes:
a) a signal generator for generating electrical signals; and,
b) a sensor for sensing electrical signals.

In another aspect, a method for use in assessing CMP function is provided, the method including, in a processing system:
a) determining a change in impedance, as a subject undergoes calf extension or exercise; and,
b) determining an indicator using the change impedance, the indicator being indicative of an ejection volume to allow assessment of CMP function.

It will be appreciated that embodiments of the invention may be used individually or in combination, and may be used for assessing CMP function as well as diagnosing the presence, absence or degree of a range of conditions in addition to and including venous insufficiency, oedema, lymphodema, body composition, or the like.

BRIEF DESCRIPTION OF THE DRAWINGS

An example of the present invention will now be described with reference to the accompanying drawings, in which.

DETAILED DESCRIPTION OF THE DRAWINGS

Figure 1:
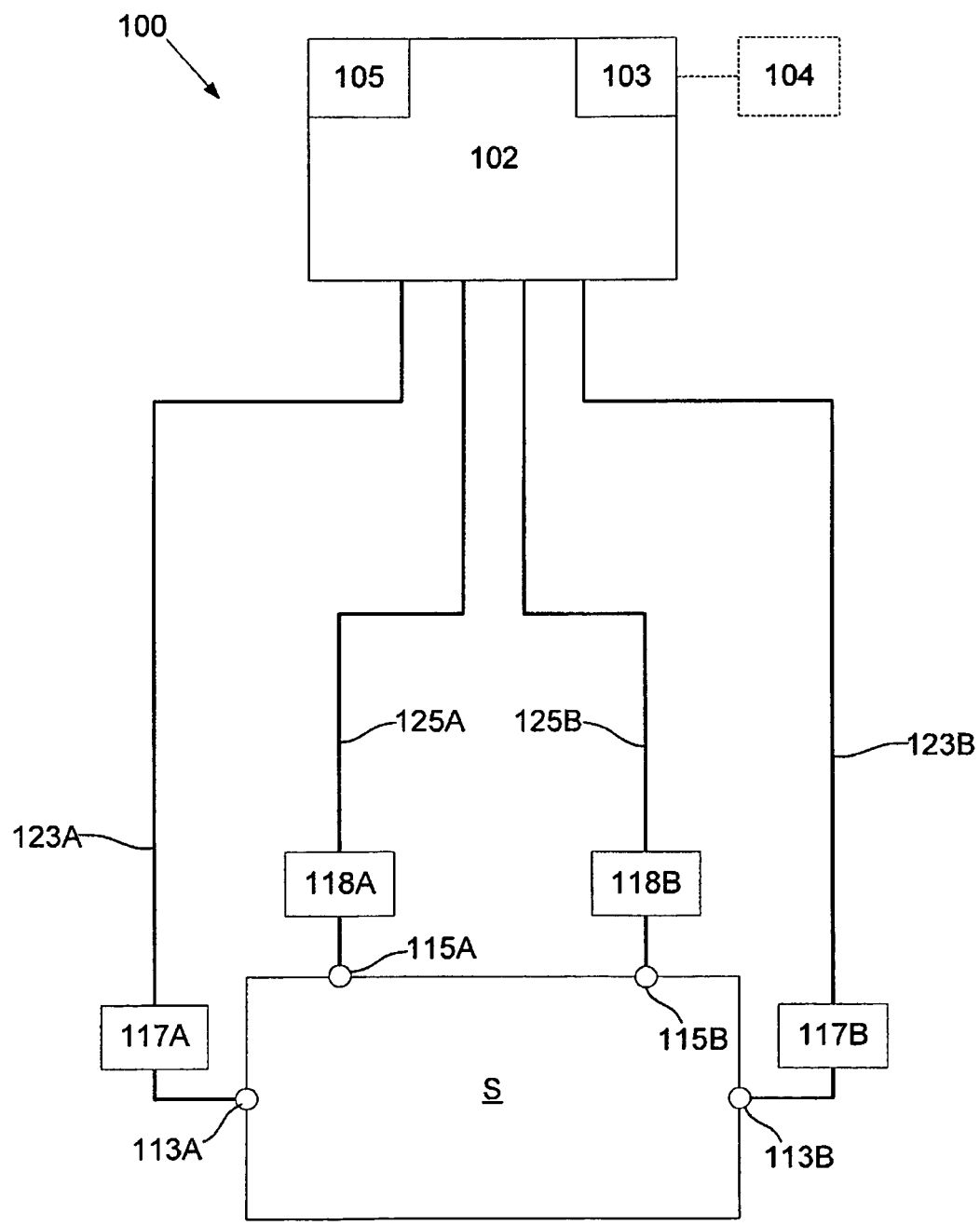
FIG. 1 is a schematic diagram of a first example of impedance measuring apparatus.

An example of apparatus suitable for performing an analysis of a subject's bioelectric impedance will now be described with reference to FIG. 1.

As shown the apparatus includes a measuring device 100 including a processing system 102, connected to one or more signal generators 117A, 117B, via respective first leads 123A, 123B, and to one or more sensors 118A, 118B, via respective second leads 125A, 125B. The connection may be via a switching device, such as a multiplexer, although this is not essential.

In use, the signal generators 117A, 117B are coupled to two first electrodes 113A, 113B, which therefore act as drive electrodes to allow signals to be applied to the subject S, whilst the one or more sensors 118A, 118B are coupled to the second electrodes 115A, 115B, which therefore act as sense electrodes, to allow signals induced across the subject S to be sensed.

The signal generators 117A, 117B and the sensors 118A, 118B may be provided at any position between the processing system 102 and the electrodes 113A, 113B, 115A, 115B, and may therefore be integrated into the measuring device 100.

However, in one example, the signal generators 117A, 117B and the sensors 118A, 118B are integrated into an electrode system, or another unit provided near the subject S, with the leads 123A, 123B, 125A, 125B connecting the signal generators 117A, 117B and the sensors 118A, 118B to the processing system 102. By performing this, the length of any connections between the signal generators 117A, 117B and the sensors 118A, 118B, and the corresponding electrodes 113A, 113B, 115A, 115B can be reduced. This minimises any parasitic capacitances between the connections, the connections and the subject, and the connections and any surrounding articles, such as a bed on which the subject is provided, thereby reducing measurement errors.

The above described system can be described as a two channel device, with each channel being designated by the suffixes A, B respectively. The use of a two channel device is for the purpose of example only, and any number of channels may be provided, as required.

An optional external interface 103 can be used to couple the measuring device 100, via wired, wireless or network connections, to one or more peripheral devices 104, such as an external database or computer system, barcode scanner, or the like. The processing system 102 will also typically include an I/O device 105, which may be of any suitable form such as a touch screen, a keypad and display, or the like.

In use, the processing system 102 is adapted to generate control signals, which cause the signal generators 117A, 117B to generate one or more alternating signals, such as voltage or current signals of an appropriate waveform, which can be applied to a subject S, via the first electrodes 113A, 113B. The sensors 118A, 118B then determine the voltage across or current through the subject S, using the second electrodes 115A, 115B and transfer appropriate signals to the processing system 102.

Accordingly, it will be appreciated that the processing system 102 may be any form of processing system which is suitable for generating appropriate control signals and at least partially interpreting the measured signals to thereby determine the subject's bioelectrical impedance, and optionally determine other information such indicators of CMP function, the presence, absence or degree of other conditions, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like, as will be described in more detail below.

In use, the first electrodes 113A, 113B are positioned on the subject to allow one or more signals to be injected into the subject S. The location of the first electrodes will depend on the segment of the subject S under study. Thus, for example, the first electrodes 113A, 113B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, assessment of CMP function, or the like.

Once the electrodes are positioned, one or more alternating signals are applied to the subject S, via the first electrodes 113A, 113B. The nature of the alternating signal will vary depending on the nature of the measuring device and the subsequent analysis being performed.

For example, the system can use Bioimpedance Analysis (BIA) in which a single low frequency signal is injected into the subject S, with the measured impedance being used directly in the determination of biological parameters, such as extracellular fluid levels, which can be used in assessing CMP function. In one example, the signal has a frequency of below 10 kHz.

In contrast Bioimpedance Spectroscopy (BIS) devices perform impedance measurements at multiple frequencies over a selected frequency range. Whilst any range of frequencies may be used, typically frequencies range from very low frequencies (4 kHz) to higher frequencies (15000 kHz). Similarly, whilst any number of measurements may be made, in one example the system can use 256 or more different frequencies within this range, to allow multiple impedance measurements to be made within this range.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

Thus, the measuring device 100 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied.

In one example, the voltage source is typically symmetrically and/or differentially arranged, with each of the signal generators 117A, 117B being independently controllable, to allow the potential across the subject to be varied. This can be performed to reduce the effects of any imbalance, which occurs when the voltages sensed at the electrodes are unsymmetrical (a situation referred to as an "imbalance"). In this instance, any difference in the magnitude of signals within the leads can lead to differing effects due to noise and interference.

Whilst applying the voltage symmetrically, can reduce the effect, this is not always effective if the electrode impedances for the two drive electrodes 113A, 113B are unmatched, which is typical in a practical environment. However, by adjusting the differential drive voltages applied to each of the drive electrodes 113A, 113B, this compensates for the different electrode impedances, and restores the desired symmetry of the voltage at the sense electrodes 115A, 115B. This can be achieved by measuring the voltages at the sense electrodes, and then adjusting the magnitude and/or phase of the applied signal to thereby balance the magnitude of the sensed voltages. This process is referred to herein as balancing and in one example is performed by minimizing the magnitude of any common mode signal.

A potential difference and/or current is measured between the second electrodes 115A, 115B. In one example, the voltage is measured differentially, meaning that each sensor 118A, 118B is used to measure the potential at each second electrode 115A, 115B and therefore need only measure half of the potential as compared to a single ended system.

The acquired signal and the measured signal will be a superposition of potentials generated by the human body, such as the ECG (electrocardiogram), potentials generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as correlating the signal. This can be achieved by multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements can be determined from the signals at each frequency using the recorded voltage across and current flow through the subject. The demodulation algorithm can then produce an amplitude and phase signal at each frequency. This can then be used to derive one or more impedance parameter values, if required.

As part of the above described process, the distance between the second electrodes may be measured and recorded. Similarly, other parameters relating to the subject (subject parameters) may be recorded, such as the height, weight, age, sex, health status, any interventions and the date and time on which they occurred. Other information, such as current medication, may also be recorded. This can then be used in performing further analysis of the impedance measurements, so as to allow assessment of CMP function, determination of the presence, absence or degree of oedema, to assess body composition, or the like.

Figure 2:
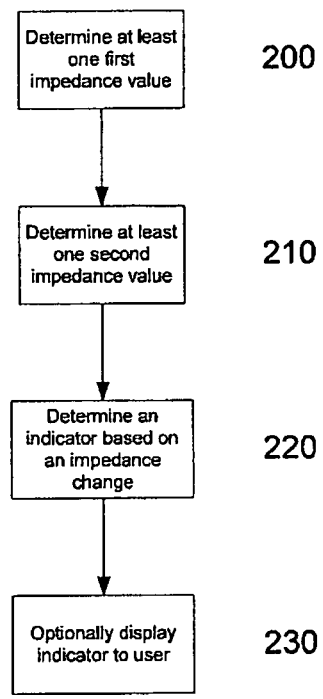
FIG. 2 is a flowchart of an example of a process for use in analysing impedance measurements.

An example of the process of analysing impedance measurements operation of the apparatus of FIG. 1 to perform this will now be described with reference to FIG. 2.

At step 200, at least one first impedance value indicative of the impedance of a segment of the subject's calf is determined, prior to the calf muscle being extended and/or exercised. This may be achieved by having the signal generators 117A, 117B, apply at least one first signal to the subject S, via the first electrodes 113A, 113B, with voltage signals being measured across a segment of the subject's calf by the sensors 118A, 118B, via the second electrodes 115A, 115B. An indication of the current flow through and voltage across the subject's calf is provided to the processing system 102, allowing the impedance, or an impedance parameter value to be determined.

At step 210, at least one second impedance value indicative of the impedance of the segment of the subject's calf is determined, following or during the calf muscle being extended and/or exercised.

In one example, this process involves measuring changes in impedance over a segment of calf muscle during a sequence of postural and/or exercise changes, such a sequence of tiptoe steps, allowing the first and second impedance values to be determined.

The impedance measurements are typically indicative of the extracellular fluid levels within the subject's calf, which is in turn inversely related to the blood volume and hence the calf volume. Accordingly, in one example, the impedance measurement is performed at a single low frequency, such as below 10 kHz, and typically at 5 kHz, allowing the indicator to be based on the measured value directly. Alternatively, multiple measurements may be performed at multiple frequencies, with the indicator being based on an appropriate impedance parameter value derived therefrom, such as the impedance at zero applied frequency $R_0$, as will be described in more detail below.

At step 220, an indicator based on an impedance change derived from a difference between the first and second impedance values, or impedance parameter values derived therefrom. The impedance of a limb or limb segment is inversely related to fluid volume and accordingly, in one example, the impedance change is indicative of the change in volume of the limb, and hence the volume of blood ejected by the CMP, known as the ejection volume (EV).

The indicator may optionally be displayed to a user at step 230 to thereby allow assessment of CMP function.

One or more other indicators may also be determined, such as the ejection fraction.

In one example, the ejection fraction is determined by having the subject rest in a supine position, with their leg elevated with foot above heart (20 cm), causing the blood to drain form the leg due to gravity, so that the volume of the calf approaches a minimum value. It will be appreciated that any suitable positioning of the subject that results in a reduction and preferably minimizing of blood pooling, may be used, and that this is for the purpose of example only. Furthermore, to help minimize blood pooling, the subject may be required to rest in the supine position for five to ten minutes. An impedance measurement is then performed to determine a measured third impedance value $R_{mv}$, which is indicative of the minimum blood volume (mv).

The subject then stands upright without bending or putting weight on leg under study, causing blood to pool in the leg. Alternatively, the subject can lean or sit with their leg hanging in a substantially vertical position, to thereby enhance the impact of blood pooling. For the purpose of the remaining description, the term standing will be understood to encompass any position that maximises or enhances pooling of blood in the subject's leg. Again, this position may be maintained for five to fifteen minutes to maximise the pooling effect.

After re-equilibration a measured fourth impedance value $R_{MV}$ is determined, which is indicative of the maximum blood volume (MV). It will be appreciated that in one example the fourth impedance value is the same as the first impedance value, and these may be determined using a single measurement.

In any event, the difference in the measured third and fourth impedance values represents the functional venous volume (VV), which can in turn be used together with the ejection volume (EV) to calculate an ejection fraction (EF). This may be performed prior to performing the calf extension/exercise process described above with respect to steps 200, 210.

In one example, any one or more of the determined indicators may be compared to a reference, to assist with the assessment of CMP function. The reference can be any suitable reference, such as values for similar indicators derived from sample populations, previous measurements for the subject, or indicators determined for the subject for different calf segments. Thus, for example, comparison to previous measured indicators for the subject can be used to perform a longitudinal analysis to determine if the subject's CMP function has improved or worsened.

Figure 3:
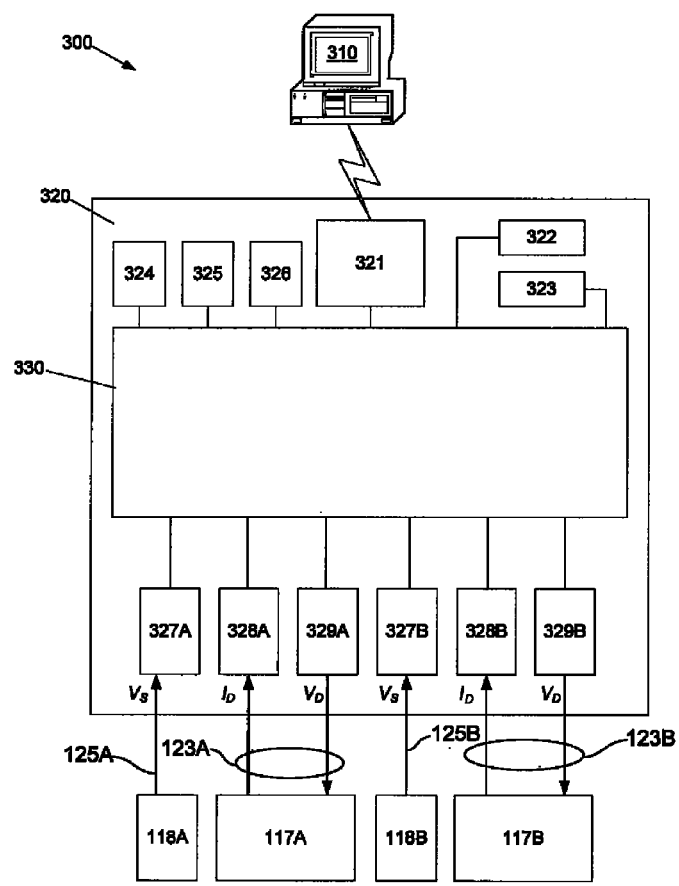
FIG. 3 is a schematic diagram of a second example of impedance measuring apparatus.

A specific example of the apparatus will now be described in more detail with respect to FIG. 3.

In this example, the measuring system 300 includes a computer system 310 and a separate measuring device 320. The measuring device 320 includes a processing system 330 coupled to an interface 321 for allowing wired or wireless communication with the computer system 310. The processing system 330 may also be optionally coupled to one or more stores, such as different types of memory, as shown at 322, 323, 324, 325, 326.

In one example, the interface is a Bluetooth stack, although any suitable interface may be used. The memories can include a boot memory 322, for storing information required by a boot-up process, and a programmable serial number memory 323, that allows a device serial number to be programmed. The memory may also include a ROM (Read Only Memory) 324, flash memory 325 and EPROM (Electronically Programmable ROM) 326, for use during operation. These may be used for example to store software instructions and to store data during processing, as will be appreciated by persons skilled in the art.

A number of analogue to digital converters (ADCs) 327A, 327B, 328A, 328B and digital to analogue converters (DACs) 329A, 329B are provided for coupling the processing system 330 to the sensors 118A, 118B and the signal generators 117A, 117B, as will be described in more detail below.

A controller, such as a microprocessor, microcontroller or programmable logic device, may also be provided to control activation of the processing system 330, although more typically this is performed by software instructions executed by the processing system 330.

Figure 4:
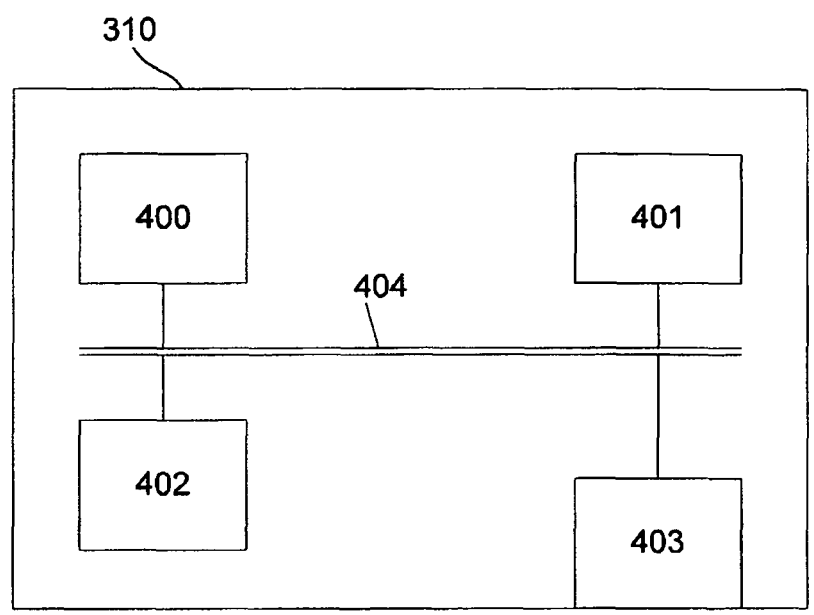
FIG. 4 is a schematic diagram of an example of a computer system.

An example of the computer system 310 is shown in FIG. 4. In this example, the computer system 310 includes a processor 400, a memory 401, an input/output device 402 such as a keyboard and display, and an external interface 403 coupled together via a bus 404, as shown. The external interface 403 can be used to allow the computer system to communicate with the measuring device 320, via wired or wireless connections, as required, and accordingly, this may be in the form of a network interface card, Bluetooth stack, or the like.

In use, the computer system 310 can be used to control the operation of the measuring device 320, although this may alternatively be achieved by a separate interface provided on the measuring device 300. Additionally, the computer system 310 can be used to allow at least part of the analysis of the impedance measurements to be performed.

Accordingly, the computer system 310 may be formed from any suitable processing system, such as a suitably programmed PC, Internet terminal, lap-top, hand-held PC, smart phone, PDA, server, or the like, implementing appropriate applications software to allow required tasks to be performed.

In contrast, the processing system 330 typically performs specific processing tasks, to thereby reduce processing requirements on the computer system 310. Thus, the processing system typically executes instructions to allow control signals to be generated for controlling the signal generators 117A, 117B, as well as the processing to determine instantaneous impedance values.

In one example, the processing system 330 is formed from custom hardware, or the like, such as a Field Programmable Gate Array (FPGA), although any suitable processing module, such as a magnetologic module, may be used.

In one example, the processing system 330 includes programmable hardware, the operation of which is controlled using instructions in the form of embedded software instructions. The use of programmable hardware allows different signals to be applied to the subject S, and allows different analysis to be performed by the measuring device 320. Thus, for example, different embedded software would be utilised if the signal is to be used to analyse the impedance at a number of frequencies simultaneously as compared to the use of signals applied at different frequencies sequentially.

The embedded software instructions used can be downloaded from the computer system 310. Alternatively, the instructions can be stored in memory such as the flash memory 325 allowing the instructions used to be selected using either an input device provided on the measuring device 320, or by using the computer system 310. As a result, the computer system 310 can be used to control the instructions, such as the embedded software, implemented by the processing system 330, which in turn alters the operation of the processing system 330.

Additionally, the computer system 310 can operate to analyse impedance determined by the processing system 330, to allow biological parameters to be determined.

Whilst an alternative arrangement with a single processing system may be used, the division of processing between the computer system 310 and the processing system 330 can provide some benefits.

Firstly, the use of the processing system 330 more easily allows the custom hardware configuration to be adapted through the use of appropriate embedded software. This in turn allows a single measuring device to be used to perform a range of different types of analysis.

Secondly, the use of a custom configured processing system 330 reduces the processing requirements on the computer system 310. This in turn allows the computer system 310 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of lymphoedema.

Thirdly, this allows the measuring device 320 to be updated. Thus for example, if an improved analysis algorithm is created, or an improved current sequence determined for a specific impedance measurement type, the measuring device can be updated by downloading new embedded software via flash memory 325 or the external interface 321.

In use, the processing system 330 generates digital control signals, which are converted to analogue voltage drive signals $V_D$ by the DACs 329, and transferred to the signal generators 117. Analogue signals representing the current of the drive signal $I_D$ applied to the subject and the subject voltage $V_S$ measured at the second electrodes 115A, 115B (shown in FIG. 1) are received from the signal generators 117 and the sensors 118 and are digitised by the ADCs 327, 328. The digital signals can then be returned to the processing system 330 for preliminary analysis.

In this example, a respective set of ADCs 327, 328, and DACs 329 are used for each of two channels, as designated by the reference numeral suffixes A, B respectively. This allows each of the signal generators 117A, 117B to be controlled independently and for the sensors 118A, 118B to be used to detect signals from the electrodes 115A, 115B respectively. This therefore represents a two channel device, each channel being designated by the reference numerals A, B.

In practice, any number of suitable channels may be used, depending on the preferred implementation. Thus, for example, it may be desirable to use a four channel arrangement, in which four drive and four sense electrodes are provided, with a respective sense electrode and drive electrode pair being coupled to each limb. In this instance, it will be appreciated that an arrangement of eight ADCs 327, 328, and four DACs 329 could be used, so each channel has respective ADCs 327, 328, and DACs 329. Alternatively, other arrangements may be used, such as through the inclusion of a multiplexing system for selectively coupling a two-channel arrangement of ADCs 327, 328, and DACs 329 to a four channel electrode arrangement, as will be appreciated by persons skilled in the art.

Figure 5:
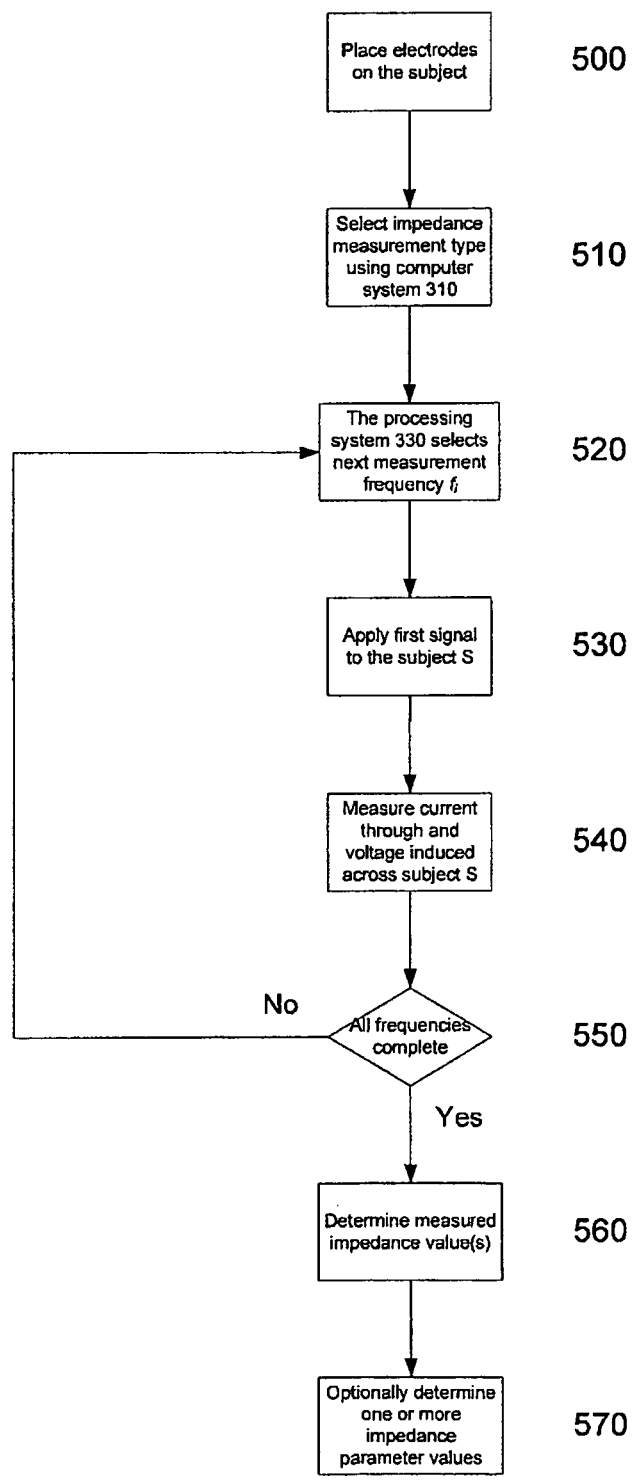
FIG. 5 is a flowchart of an example of a process for performing impedance measurements.

An example of the process for performing impedance measurements will now be described with reference to FIG. 5.

At step 500, the electrodes are positioned on the subject as required. The general arrangement to allow impedance of a leg to be determined is to provide drive electrodes 113A, 113B on the hand at the base of the knuckles and on the feet at the base of the toes, on the side of the body being measured. Sense electrodes 115A, 115B are also positioned on the calf as required.

At step 510, an impedance measurement type is selected using the computer system 310, allowing the processing system to determine an impedance measurement protocol, and configure the processing system 330 accordingly. This is typically achieved by configuring firmware or software instructions within the processing system 330, as described above.

At step 520, the processing system 300 selects a next measurement frequency $f_i$, and causes the signal generators 117A, 117B to apply a first signal to the subject at the selected frequency at step 530. At step 540, the signal generators 117A, 117B and sensors 118A, 118B provide an indication of the current through and the voltage across the subject to the processing system 330.

At step 550, the processing system 330 determines if all frequencies are complete, and if not returns to step 520 to select the next measurement frequency. At step 560, one or more measured impedance values are determined, by the computer system 310, the processing system 330, or a combination thereof, using the techniques described above. One or more impedance parameter values may optionally be derived at step 570.

Figure 6A:
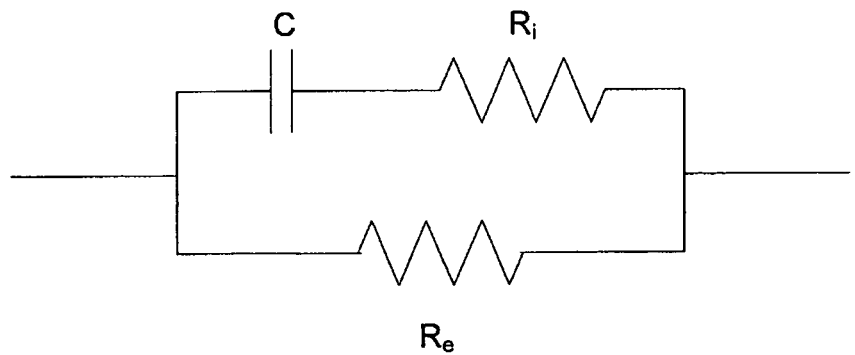
FIG. 6A is a schematic of an example of a theoretical equivalent circuit for biological tissue.

In this regard, FIG. 6A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \quad (1)$$

Accordingly, the impedance of the equivalent circuit of FIG. 6A at an angular frequency $\omega$, where $\omega=2\pi*$frequency, is given by:

$$Z = R_\infty + \frac{R_0 - R_\infty}{1 + (j\omega\tau)} \quad (2)$$

where:
$R_\infty$=impedance at infinite applied frequency
$R_0$=impedance at zero applied frequency=$R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (3)$$

where:
$\alpha$ has a value between 0 and 1 and can be thought of as an indicator of the deviation of a real system from the ideal model.

Figure 6B:
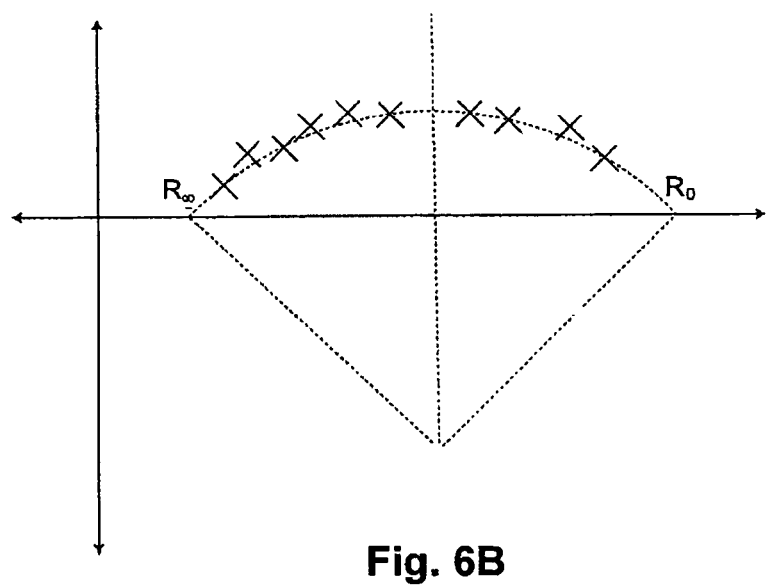
FIG. 6B is an example of a locus of impedance known as a Wessel plot.

The values of impedance parameters $R_0$, $R_\infty$ or $Z_c$ may be determined in any one of a number of manners such as by:
solving simultaneous equations based on the impedance values determined at different frequencies;
using iterative mathematical techniques;
extrapolation from a "Wessel plot" similar to that shown in FIG. 6B;
performing a function fitting technique, such as the use of a polynomial function.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values such as $R_0$, $Z_c$, and $R_\infty$ may be used.

Figure 7A:
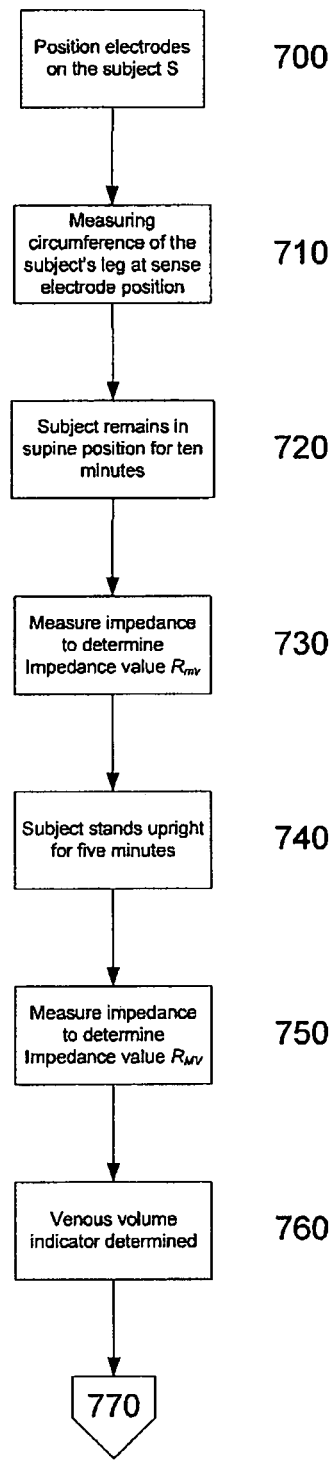
FIGS. 7A and 7B are a flowchart of a first specific example of a process for analysing impedance measurements to allow assessment of CMP function.
Figure 7B:
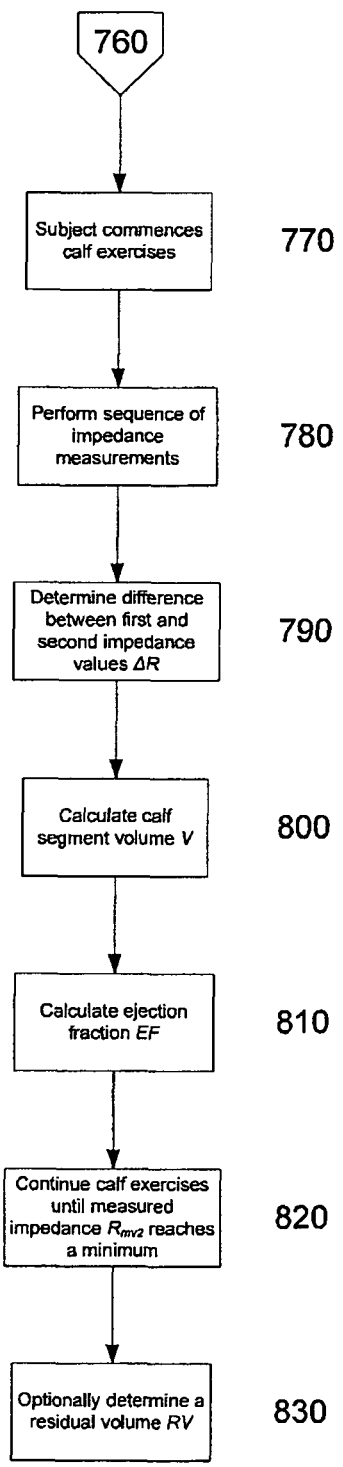

A first specific example of a process for analyzing impedance measurements to allow assessment of CMP function will now be described with reference to FIGS. 7A and 7B.

In this example, BIA is used to measure changes in impedance over a segment of the leg in the region of the calf muscle as the subject performed the standard sequence of postural and exercise changes used in APG.

At step 700, electrodes are positioned on the subject. In one example, silver-silver chloride ECG type electrodes were used, with electrode sites were cleaned with alcohol swabs prior to attachment of the electrodes. The drive electrodes 113A, 113B are positioned at the base of the toes and the base of the fingers, with the sense electrodes being located 7 and 20 cm distal from the crease at the back of the knee along the mid-line through the calf muscle.

At step 710 the circumference of the leg in the transverse plane at the point of attachment of the sense electrodes can be recorded. This is typically achieved by measurement, with the resulting value being provided to the measuring device 100, using the input 105.

At step 720, the subject assumes a supine position with the leg to be studied elevated such that the foot is above the level of the heart (20 cm). The subject remains in this position for about ten minutes, to allow the volume of blood in the leg to approach a minimum value as the veins empty of excess blood that has pooled in the legs due to gravity when the subject is upright. At step 730 an impedance measurement process is performed, with the resulting impedance value $R_{mv}$ representing the minimum venous volume (mv).

The subject returns to the upright position at step 740, taking care not to put any weight on the leg under study. There is an increase in volume because of venous filling, and after about five minutes the leg volume reaches a maximum. At step 750, an impedance measurement process is performed, with the resulting impedance value $R_{MV}$ representing the maximum venous volume (MV).

At step 760, a venous volume indicator is determined by measuring device 100. The indicator is based on the difference between the maximum and minimum venous volumes, and therefore represents the functional venous volume (VV), which can be determined using the following equation:

$$VV = \frac{\rho_b L^2 (R_{mv} - R_{MV})}{R_{mv} R_{MV}} \quad (4)$$

where:
$\rho_b$ is the resistivity of blood; and,
L is the length of the segment.

At step 770, the subject commences calf exercises, such as tiptoe movements, to cause fluid to be ejected by the action of the CMP. During this process, at step 780, a sequence of impedance measurements are performed to allow a sequence of impedance values to be determined.

At step 790, first and second impedance values are determined from the sequence of impedance values, with the difference between these representing a change in impedance $\Delta R$ indicative of the ejection volume (EV). In one example, the first impedance value can be based on the maximum volume impedance $R_{MV}$, determined at step 750 above, with the second impedance value being determined based on a mean impedance value determined during the calf exercise.

The volume of ejected blood (EV) may be calculated from the equation:

$$EV = \frac{-\rho_b L^2 \Delta R}{R_{MV}^2} \quad (4)$$

where:
$\rho_b$ is the resistivity of blood;
L is the length of the segment; and, $\Delta R$ is the change in resistance related to the change in blood volume.

At step 800, the volume (V) of the leg segment being measured is calculated from the equation:

$$V = (Ca^2 + CaCb + Cb^2)\frac{L}{12\pi} \quad (5)$$

where:
L is the distance between the sense electrodes;
Ca and Cb are the circumferences at the two electrode attachment points.

At step 810, an ejection fraction (EF) can be calculated from the following equation:

$$EF = \left(\frac{EV}{VV}\right) \times 100\% \quad (6)$$

Additionally, using the volume and ejection volume, allows blood flow per 100 ml of tissue to be calculated.

At step 820, calf exercises can be continued until a measured impedance value $R_{mv2}$ reaches a minimum value. This allows a residual volume (RV), to be determined based on the difference between the measured impedance value $R_{mv2}$ and the impedance value $R_{mv}$ at step 830.

In a second specific example, the subject reclines supine on the examination couch with the right heel resting on a 20 cm high block, with the impedance being recorded for 30 sec. The subject remains recumbent for 10 min and impedance was again recorded for 30 sec.

The subject then stands erect, 5 sec after recording commenced, by moving both legs over the side of the examination couch taking care not to bend the ankle or knee of the right leg. The subject then lowered themselves onto the floor taking the weight on the left leg until they were able to stand erect with the weight evenly distributed on both feet. Assuming the standing position from recumbency took approximately 15 sec. Recording continued for a further 10 sec with the subject standing with the weight evenly distributed on both feet.

The subject remained in this position for 5 min. At this point recording was recommenced with the subject remaining standing still for 5 sec and then performing one tiptoe movement followed eight seconds later by the subject performing 10 repeated tiptoe movements in 10 seconds and then remaining standing until the recording finished, approximately 10 sec.

Changes in resistance with time were used to calculate ejection fraction, as described above, with the mean resistance recorded during the subject's recumbency reflected minimum blood volume (mv) and the resistance recorded on attaining the upright position corresponded to the maximum venous volume (MV). The difference in these values represents functional venous volume (VV). Ejected blood volume (EV) is represented by the mean value of the resistance during the 10 tiptoe movements minus the resistance of the maximum volume. Thus ejection fraction (EF) may be calculated according to equation 6.

Figure 8A:
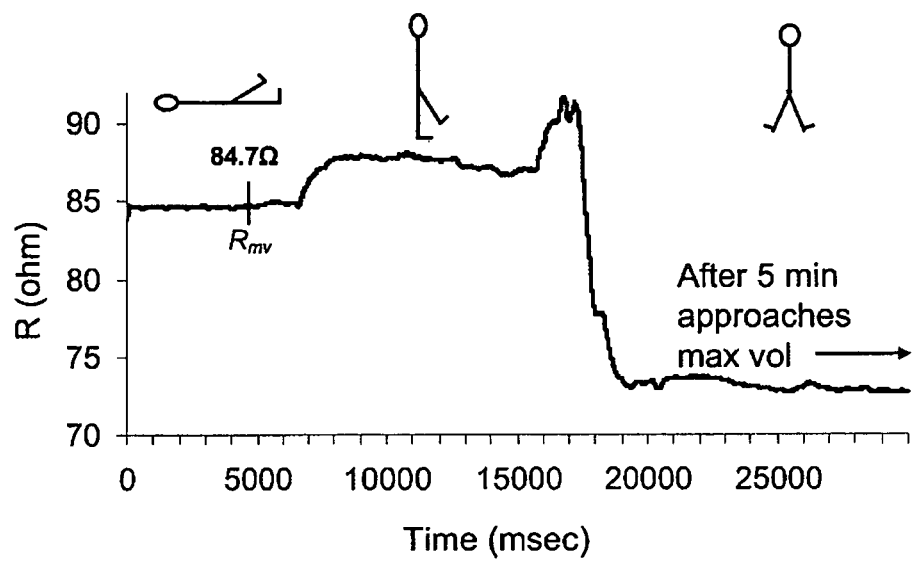
FIG. 8A is a graph showing example measurements as a subject transfers from recumbency with the leg elevated to the fully upright standing position.
Figure 8B:
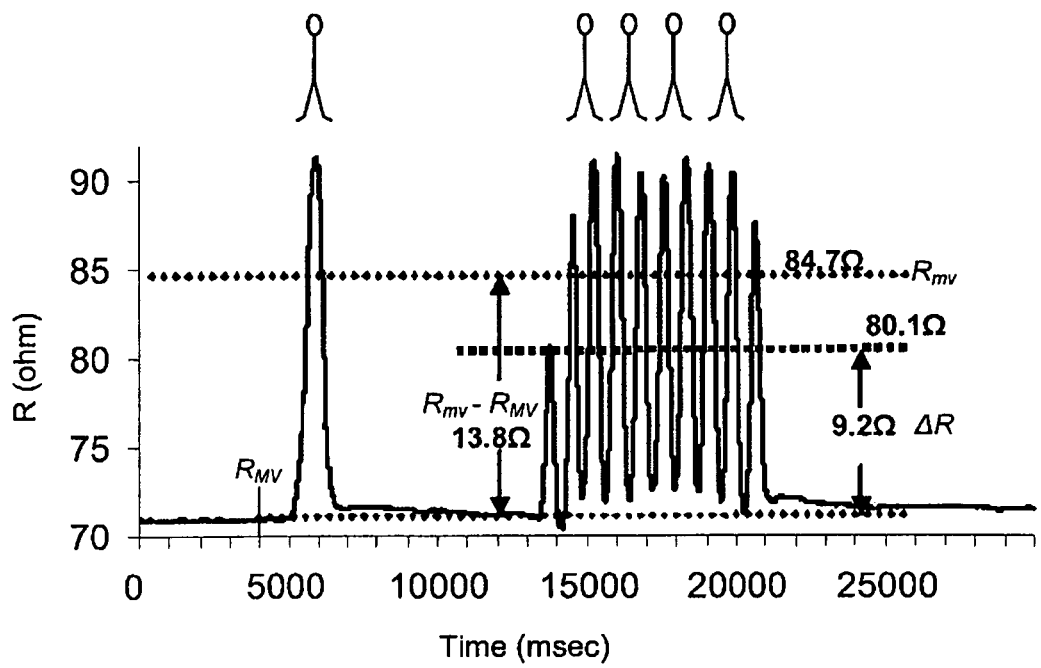
FIG. 8B is a graph showing example measurements during the tiptoe events; and,
FIG. 9 are graphs showing the similarity between change in measured impedance and change in limb segment volume as determined using APG.

The time course of change of resistance for a typical subject is presented in FIGS. 8A and 8B.

FIG. 8A shows the change in resistance R as the subject transfers from recumbency with the leg elevated (approximately first 5 sec of recording) to the fully upright standing position with the weight evenly distributed on both feet attained after approximately 18 sec. The resistance $R_{mv}$ is shown.

FIG. 8B shows the change in resistance ΔR during the tiptoe events. Resistance increases with each tiptoe movement. Mean resistance during these 10 tiptoe movements was used to determine the change in resistance ΔR used in determining the ejected volume (EV).

In this example, the ejection fraction for this subject was 66.6%. The upper circumference of the calf for this subject was 36 cm and the lower circumference was 24 cm resulting in the volume of blood ejected from the calf being 5.9 ml per 100 ml of tissue.

Figure 9:
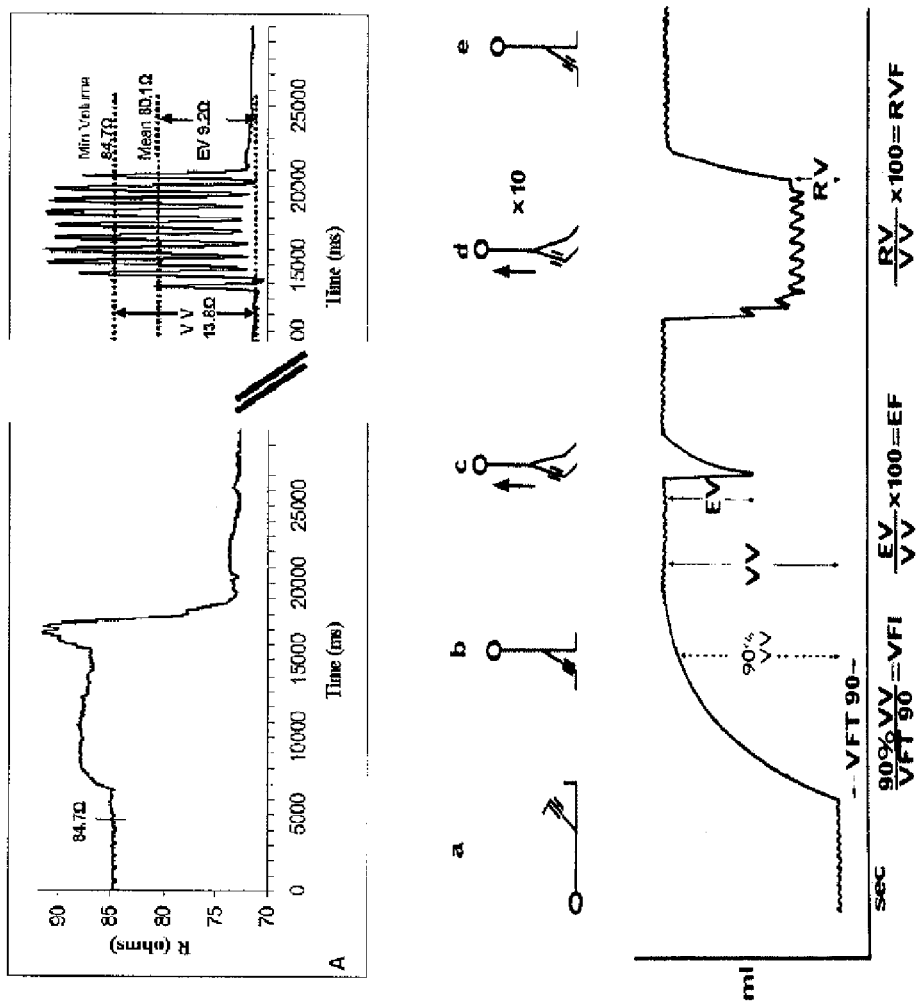

It can be seen from FIG. 9, which shows a comparison of the results of FIGS. 8A and 8B against equivalent volume measurements made using APG. As shown the variation in resistance caused by calf exercise is inversely proportional to the change in volume measured using APG, thereby highlighting that impedance measurement can be used as a reliable substitute for APG.

Furthermore, changes in fluid levels can typically be detected using impedance measurements before the fluid level changes have a noticeable impact on limb volume, thereby making the impedance measurement process more sensitive than other techniques such as SPG or APG.

Impedance measuring apparatus is generally easier to use and more able to produce consistent results without extensive calibration, this makes this a useful method for determining an indicator that can be used in assessing CMP function.

Examples of results for duplicate measurements for nine volunteer subjects (age 21-59 years, 6 males and 3 females) are presented in Tables 1 and 2.

TABLE 1

Ejection Fraction

| Subject | 1 EF % | 2 EF % |
|---|---|---|
| 1 | 33.3 | 40.7 |
| 2 | 49.3 | 63.4 |
| 3 | 392 | 158 |
| 4 | 81 | 91.5 |
| 5 | 66.6 | 55.3 |
| 6 | 37.5 | 54.5 |
| 7 | 62.2 | 86 |
| 8 | 148 | 130 |
| 9 | 41 | 34 |

TABLE 2

Ejection Volume ml/100 ml tissue

| Subject | 1 EV ml/ 100 ml tissue | 2 EV ml/ 100 ml tissue |
|---|---|---|
| 1 | 3.8 | 4.4 |
| 2 | 2.5 | 3.2 |
| 3 | 5.9 | 6.3 |
| 4 | 5.2 | 6.0 |
| 5 | 5.9 | 4.8 |
| 6 | 2.2 | 2.6 |
| 7 | 4.8 | 5.0 |
| 8 | 4.8 | 4.7 |
| 9 | 4.6 | 4.6 |

Reference values determined from studies of sample populations for APG indicate that an EF>60% is good, with an EF<40% being poor.

Accordingly, in this study 6 out of 9 subjects had EF values>60%, which is generally considered as good, and 3 had EF values between 40% and 60%, is generally considered reasonable.

Two of the subjects have EF values in excess of 100%, which is typically caused by a large calf muscle that results in more blood being massaged out of the veins by muscle pumping during the tiptoe movement than simply under the influence of gravity while supine with the leg elevated.

Ejection volumes for all subjects were also within the normal range, which for typical healthy subjects lies between 2 and 6 ml per 100 ml of tissue. These observations are consistent with all subjects being healthy without any indications of venous insufficiency, varicose veins or leg ulcers.

Accordingly, BIA or BIS can be used to measure ejection fraction and ejection volume, allowing CMP function to be assessed. BIA measurements are less technically challenging than the alternatives such as APG, use less expensive equipment, are amenable to use in patients with medical conditions of the leg that requires pressure bandaging that would preclude the use of other methods without removal of the bandages. Additionally, impedance measurement techniques are generally more influenced by blood volume changes than APG or SPG measurements, thereby making the process more sensitive than SPG or APG measurements.

In the above described examples, the term resistance generally refers to measured impedance values or impedance parameter values derived therefrom.

The term processing system is intended to include any component capable of performing processing and can include any one or more of a processing system and a computer system.

Persons skilled in the art will appreciate that numerous variations and modifications will become apparent. All such variations and modifications which become apparent to persons skilled in the art, should be considered to fall within the spirit and scope that the invention broadly appearing before described.

Thus, the above described protocol is for the purpose of example only, and alternative methods can be used. For example, electrodes can be provided in different positions such as lower on the leg just above the ankle rather than over the mid-point of the calf. Additionally and/or alternatively, the type of movement may be changed from tiptoes to knee bends.

Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used in determining biological indicators, which in turn can be used for diagnosing the presence, absence or degree of a range of conditions and illnesses, including, but not limited to via, oedema, lymphodema, body composition, or the like.

Furthermore, whilst the above described examples have focussed on the application of a voltage signal to cause a current to flow through the subject, this is not essential and the process can also be used when applying a current signal.

It will also be appreciated that the term impedance measurement covers admittance and other related measurements.

I claim:

1. A method for use in analysing impedance measurements performed on a subject for use in diagnosing the presence, absence, or degree of venous insufficiency in the subject, the method including, in a processing system:

determining a change in impedance, caused by calf extension of the subject or by exercise by the subject;
determining an indicator using the change in impedance, the indicator being indicative of an ejection volume to allow assessment of calf muscle pump (CMP) function, wherein the method further includes, in the processing system, determining the ejection volume using the formula:

$$EV = \frac{-\rho_b L^2 \Delta R}{R_{MV}^2}$$

where:
$\rho_b$ is the resistivity of blood;
L is a length of a segment of a calf of the subject;
$\Delta R$ is the change in impedance; and
$R_{MV}$ is a maximum volume impedance value; and
displaying the indicator via the processing system to a user to thereby allow assessment of CMP function, wherein, at least one of the indicator or CMP function is used in the diagnosis of the presence, absence or degree of venous insufficiency.

2. A method according to claim 1, wherein the method includes, in a processing system:
determining a first impedance value prior to calf extension;
determining a second impedance value following or during calf extension; and,
determining the impedance change using the first and second impedance values.

3. A method according to claim 1, wherein the method includes, in a processing system:
determining a third impedance value with the subject in a supine position;
determining a fourth impedance value with the subject in a standing position;
determining a second impedance change using the third and fourth impedance values; and
determining a second indicator using the second impedance change, the second indicator being indicative of a venous volume for use in assessment of CMP function.

4. A method according to claim 3, wherein:
the third impedance value is a minimum volume impedance value $R_{mv}$; and,
the fourth impedance value is a maximum volume impedance value $R_{MV}$.

5. A method according to claim 4, wherein the method includes, in a processing system, determining a functional venous volume using the formula:

$$VV = \frac{\rho_b L^2 (R_{mv} - R_{MV})}{R_{mv} R_{MV}}$$

where:
$R_{mv}$ is the third impedance value which is a minimum volume impedance value;
$R_{MV}$ is the fourth impedance value which is a maximum volume impedance value;
$\rho_b$ is the resistivity of blood; and,
L is the length of the segment of a calf of the subject.

6. A method according to claim 1, wherein the method includes, in a processing system, determining at least one of:
a venous volume; and
an ejection fraction.

7. A method according to claim 1, wherein the method includes, in a processing system:
comparing an indicator to a reference; and,
providing an indication of the results of the comparison to allow assessment of CMP function.

8. A method according to claim 7, wherein the reference includes at least one of:
an indicator determined for another calf segment of the subject;
a indicator determined from a sample population; and,
a previous indicator determined for the subject.

9. A method according to claim 1, wherein the impedance is determined at a frequency of less than 10 kHz.

10. A method according to claim 1, wherein the method includes, in the processing system:
determining a plurality of impedance values; and,
determining at least one impedance parameter value from the plurality of impedance values.

11. A method according to claim 10, wherein at least one of the at least one impedance parameter value includes any one of:
$R_0$ which is the resistance at zero frequency;
$R_\infty$ which is the resistance at infinite frequency; and,
$Z_c$ which is the resistance at a characteristic frequency.

12. A method according to claim 1, wherein determining a change in impedance includes, in the processing system, causing the change in impedance to be measured by:
causing one or more electrical signals to be applied to the subject using a first set of electrodes;
measuring electrical signals across a second set of electrodes applied to the subject in response to the applied one or more signals; and,
determining from the applied signals and the measured signals at least one measured impedance value.

13. Apparatus for use in analysing impedance measurements performed on a subject for use in diagnosing the presence, absence, or degree of venous insufficiency in the subject, the apparatus including a processing system configured to:
determine a change in impedance, caused by calf extension of a subject or by exercise by a subject;
determine an indicator using the change in impedance, the indicator being indicative of an ejection volume to allow assessment of calf muscle pump (CMP) function, wherein the processing system is further configured to determine the ejection volume using the formula:

$$EV = \frac{-\rho_b L^2 \Delta R}{R_{MV}^2}$$

where:
$\rho_b$ is the resistivity of blood;
L is a length of a segment of a calf of the subject;
$\Delta R$ is the change in impedance; and
$R_{MV}$ is a maximum volume impedance value; and
display the indicator via the processing system to a user to thereby allow assessment of CMP function, wherein, the indicator is used in the diagnosis of the presence, absence or degree of venous insufficiency.

14. Apparatus according to claim 13, wherein the processing system is further configured to:
cause one or more electrical signals to be applied to the subject using a first set of electrodes;

measure electrical signals across a second set of electrodes applied to the subject in response to the applied one or more signals; and, determine from the applied signals and the measured signals at least one measured impedance value.

15. Apparatus according to claim 14, wherein the apparatus includes:
a signal generator for generating electrical signals; and,
a sensor for sensing electrical signals.

16. A method for use in analysing impedance measurements performed on a subject for use in diagnosing the presence, absence, or degree of venous insufficiency in the subject, the method including:

applying, using a signal generator, one or more electrical signals to the subject using a first set of electrodes;

measuring, using a sensor, electrical signals across a second set of electrodes applied to the subject in response to the applied one or more signals, and in a processing system:

determining a change in impedance, caused by calf extension of a subject or by exercise by a subject, the change in impedance determined from the applied signals and the measured signals; and, determining an indicator using the change in impedance, the indicator being indicative of an ejection volume to allow assessment of calf muscle pump (CMP) function, wherein the method further includes, in the processing system, determining the ejection volume using the formula:

$$EV = \frac{-\rho_b L^2 \Delta R}{R_{MV}^2}$$

where:
$\rho_b$ is the resistivity of blood;
L is a length of a segment of a calf of the subject;
$\Delta R$ is the change in impedance; and,
$R_{MV}$ is a maximum volume impedance value; and displaying the indicator via the processing system to a user to thereby allow assessment of CMP function, wherein, at least one of the indicator or CMP function is used in the diagnosis of the presence, absence or degree of venous insufficiency.

* * * * *